United States Patent [19]

Guttmann et al.

[11] Patent Number: 4,746,641

[45] Date of Patent: May 24, 1988

[54] AMMOXIDATION OF PARAFFINS AND CATALYSTS THEREFOR

[75] Inventors: Andrew T. Guttmann, Maple Heights; Robert K. Grasselli, Aurora; James F. Brazdil, Mayfield Village, all of Ohio

[73] Assignee: Standard Oil Company, Cleveland, Ohio

[21] Appl. No.: 724,226

[22] Filed: Apr. 17, 1985

Related U.S. Application Data

[63] Continuation-in-part of Ser. No. 643,208, Aug. 22, 1984, abandoned.

[51] Int. Cl.$^4$ .................. B01J 21/02; B01J 27/198; B01J 27/057; B01J 21/08

[52] U.S. Cl. .................. 502/202; 502/204; 502/206; 502/207; 502/209; 502/215; 502/241; 502/246; 502/247; 502/306; 502/307; 502/311; 502/312; 502/324; 502/337; 502/338; 502/344; 502/353

[58] Field of Search .......... 502/202, 204, 206, 207, 502/209, 215, 241, 246, 247, 306, 307, 311, 313, 324, 337, 338, 344, 353

[56] References Cited

U.S. PATENT DOCUMENTS

| | | | |
|---|---|---|---|
| 3,358,020 | 12/1967 | Hendrickx | 502/312 X |
| 3,424,781 | 1/1969 | Capp et al. | 502/312 X |
| 3,542,843 | 11/1970 | Yoshino et al. | 502/206 X |
| 3,554,931 | 1/1971 | Brown | 502/353 X |
| 3,591,620 | 7/1971 | Yoshino et al. | 502/207 X |
| 3,637,797 | 1/1972 | Decker et al. | 502/312 X |
| 3,657,155 | 4/1972 | Yoshino et al. | 502/247 X |
| 3,668,147 | 6/1972 | Yoshino et al. | 502/204 X |
| 3,670,017 | 6/1972 | Ball et al. | 502/312 X |
| 3,716,496 | 2/1973 | Yoshino et al. | 502/215 |
| 3,725,472 | 4/1973 | Kawano et al. | 502/312 X |
| 3,860,534 | 1/1975 | Harris et al. | 502/353 |
| 3,873,595 | 3/1975 | Lüssling et al. | 502/353 X |
| 3,903,149 | 9/1975 | Kodowaki et al. | 502/312 X |
| 3,904,653 | 9/1975 | Milberger et al. | 502/312 X |
| 3,984,353 | 10/1976 | Sergunkin et al. | 502/311 X |
| 3,988,359 | 10/1976 | Saito et al. | 502/204 X |
| 4,052,418 | 10/1977 | Suresh et al. | 502/353 X |
| 4,075,231 | 2/1978 | Dolhyj et al. | 502/204 X |
| 4,076,731 | 2/1978 | Dolhyj et al. | 502/202 X |
| 4,083,804 | 4/1978 | Saito et al. | 502/209 X |
| 4,138,366 | 2/1979 | Shaw et al. | 502/209 X |
| 4,165,300 | 8/1979 | Dolhyj et al. | 502/312 X |
| 4,219,671 | 8/1980 | Slinkard et al. | 502/338 X |
| 4,234,461 | 11/1980 | Suresh et al. | 502/344 X |
| 4,290,920 | 9/1981 | Suresh et al. | 502/353 X |
| 4,336,205 | 1/1982 | Onishi et al. | 502/311 X |
| 4,339,598 | 7/1982 | Guttmann et al. | 502/247 X |
| 4,410,450 | 10/1983 | Sasaki et al. | 502/324 X |
| 4,419,272 | 12/1983 | Wolfgang et al. | 502/324 X |
| 4,504,599 | 3/1985 | Sasaki et al. | 502/324 X |
| 4,508,848 | 4/1985 | Dolhyj et al. | 502/353 X |
| 4,524,236 | 6/1985 | McCain | 502/324 X |

FOREIGN PATENT DOCUMENTS

| | | | |
|---|---|---|---|
| 0896536 | 3/1972 | Canada | 502/353 |
| 2124639 | 12/1971 | Fed. Rep. of Germany | 502/204 |
| 46-3459 | 1/1971 | Japan | 502/312 |
| 1176233 | 1/1970 | United Kingdom | 502/353 |
| 0189771 | 3/1967 | U.S.S.R. | 502/312 |

Primary Examiner—Helen M. S. Sneed
Assistant Examiner—William G. Wright
Attorney, Agent, or Firm—C. S. Lynch; D. J. Untener; L. W. Evans

[57] ABSTRACT

Disclosed is a process for ammoxidation of paraffins containing 2-5 C atoms over a vanadium-antimony oxide catalyst, the catalyst, and a precursor slurry for making such catalyst.

5 Claims, No Drawings

AMMOXIDATION OF PARAFFINS AND CATALYSTS THEREFOR

This application is a continuation-in-part of parent application Ser. No. 643,208 filed Aug. 22, 1984, now abandoned.

This invention relates to the catalytic ammoxidation of paraffins containing from 2 to 5 carbon atoms to $\alpha,\beta$ unsaturated nitriles, especially paraffins containing 3 to 4 carbon atoms. Most important is the ammoxidation of propane to acrylonitrile.

Because of the price differential between propylene and propane an ecomomic incentive exsists for the development of a viable catalytic process for conversion of propane to acrylonitrile.

Earlier attempts to develop an efficient process for the ammoxidation of propane to acrylonitrile produced either insufficient yields or processes that necessitated adding halogen promotors to the feed. The later procedure would require not only reactors made of special corrosion resistant materials, but also the quantitative recovery of the promotor. The added costs thus eliminated the advantage of the propane/propylene price differential.

It is thus an object of the present invention to provide an improved process for the ammoxidation of paraffins to unsaturated nitriles.

It is a further object of the invention to provide new catalysts for such reaction.

It is still another object of the present invention to provide improved methods of preparing such catalysts, and precursors for such catalysts.

Still another object is to provide an improved catalytic ammoxidation process for making unsaturated nitriles from lower paraffins without the use of halogen promotors.

Other objects, as well as aspects, features and advantages of the present invention will become apparent from a study of the accompanying disclosure and the claims.

These and other objects are achieved by the present invention according to one aspect of which there is provided a process for the ammoxidation of paraffins containing 2 to 5 carbon atoms by the catalytic reaction of such paraffins with oxygen and ammonia by catalytic contact with an essentially bismuth free complex metal oxide catalyst having the ingredients and the proportions which are represented by the following empirical formula:

$$VSb_mA_aB_bC_cO_x,\qquad\text{formula (1)}$$

where

A is one or more of W, Sn, Mo, B and Ge;
B is one or more of Fe, Co, Ni, Cr, Mn, Cu, Zn, Se, Te, Pb and As;
C is one or more of an alkali metal, Ca, Sr, Ba and Tl
and where m is greater than 1 and up to 20 (usually 2-10, most usually 3-7); a is 0-10; b is 0-5; c is 0-1; a is equal to or less than m; b is equal to or less than m; wherein x is determined by the oxidation state of the other elements, and wherein the antimony has an average valency higher than +3 and the vanadium has an average valency lower than +5, wherein crystalline $Sb_2O_4$ is present in said catalyst, and wherein the foregoing catalyst is on a inorganic oxide support material. All of the subscripts in formula (1) are of course atoms.

A now preferred support material is alumina or silica-alumina, as further discussed herein.

It should be noted that the present ammoxidation reaction is effected in the substantial absence of halogen or sulfur or compounds thereof. Preferably also, a halide or halogen is not employed in the preparation of the catalyst precursor of the invention.

The present process is especially useful in the ammoxidation of propane and isobutane.

Especially useful catalyst compositions of the foregoing description are those in which a is at least 1 and includes at least 1 atom of W.

According to the present invention, in a preferred embodimemt, the foregoing catalysts are prepared under conditions such that in the final composition the average oxidation state of vanadium preferably approaches +3. One method of the present invention for preparing the catalysts is by a redox reaction between a compound of trivalent antimony such as $Sb_2O_3$ and a compound of pentavalent vanadium such as $V_2O_5$, during which the antimony is oxidized and the vanadium reduced, presumably according to the equation $$Sb_2O_3+V_2O_5\rightarrow 2VSbO_4 \qquad\text{Equation (1)}$$

The product is a vanadium antimonate approaching the composition $VSbO_4$ with vanadium predominately present as $V^{3+}$ and antimony as $Sb^{5+}$.

The foregoing redox reaction was described by Birchall and Sleight (*Inorganic Chem.* 15, 868–70 [1976]) and by Berry et al. (*J. Chem. Soc. Dalton Trans.*, 1983, 9–12), who effected the reaction by heating a dry mixture of the above reactants at temperatures above 600° C. Berry characterized the product as $VSb_{1-y}O_{4-1.5y}$ where $0<y>0.1$. This product had a tetragonal rutile-type crystalline structure with a unique x-ray diffraction pattern.

According to one aspect of the invention we have now found that the redox reaction can successfully and more conveniently be carried out in an aqueous medium, at a lower temperature by heating at a temperature of at least 80° C. and up to 200° C., for instance, by heating an aqueous dispersion of a $V^{5+}$ compound, such as $NH_4VO_3$ or $V_2O_5$, with an $Sb^{3+0}$ compound in excess over that called for Equation (1), such as by reacting $Sb_2O_3$ and $NH_4VO_3$ (or $V_2O_5$). To prepare the final catalyst, this is followed by evaporation, drying and then calcining the product in an oxygen-containing atmosphere, such as air, at from 350° to 700° or 750° C., usually 400° to 600° C. The length of the calcination period may range from 30 minutes to 12 hours, but satisfactory catalysts are usually obtained by calcination at such temperatures for a period of from 1 to 5 hours. Surprisingly, the vanadium antimonate obtained by this preferred aqueous redox procedure has an x-ray diffraction pattern identical to that of the compound prepared by Berry et al. at a much higher temperature by Berry's solid state reaction.

At least part of the excess of trivalent antimony compound, such as $Sb_2O_3$, is oxidized to $Sb_2O_4$ during the calcination in a molecular oxygen containing atmosphere, such as air. The presence in the finished catalyst of the excess antimony oxide as $Sb_2O_4$ results in superior catalytic performance.

The ingredients of the catalysts other than vanadium and antimony (and of course part of the oxygen) are preferably incorporated after completion of the foregoing redox reaction.

According to one aspect of the present invention there is provided a catalyst precursor which comprises an aqueous slurry of the redox reaction product of a $V^{5+}$ compound and an $Sb^{3+}$ compound where the $Sb^{3+}$ compound is in excess, said redox reaction product having the empirical formula $$VSb_mO_x, \qquad \text{formula (2)}$$

in admixture with a solid, particulate inorganic oxide support material, where m is $>1$ and up to 20 and wherein the unreacted antimony is in the form of antimony trioxide, the V has an average valence less than $+5$ and the reacted Sb has an average valence more than $+3$, and wherein the atoms of Sb over $m=1$ are present at least in part as $Sb_2O_3$ and the support material is from 10 to 90 weight percent, usually from 20–75 weight percent, of the total slurry solids on a dry oxide basis.

Usually, in the above precursor slurries m is 2–10, more usually 3–7.

The catalyst precursor slurry can be dried and calcined in a molecular oxygen containing gas at temperatures of 350° to 700° C., usually 400° to 600° C., to produce a catalyst useful in the process of the invention for ammoxidizing $C_2$ to $C_5$ paraffins. The additives A, B and/or C, if any, can be added in the slurry after the redox reaction, or the solid particles containing the vanadium and antimony values after separation from the aqueous medium can be coated or impregnated in a known manner with such additives at any suitable stage prior to final calcination of the catalyst.

It should be noted that when the oxidation of the unreacted excess $Sb_2O_3$ during calcination is prevented by an exclusion of oxygen, such as by calcination in a nitrogen atmosphere, a very inferior catalyst results.

If vanadium-antimony catalysts are prepared by using pentavalent vanadium and pentavalent antimony compounds, thus eliminating the redox reaction, both the vanadium and antimony remain in the high oxidation state and the resulting catalyst is very inferior, with or without additives. It has also been found that inferior catalysts are made when the vanadium-antimony compound is made by reacting $Sb_2O_3$ and $V_2O_5$ (or other $V^{5+}$ compound) in the presence of compounds that may act as oxidizing or reducing agents, such as nitric acid, nitrates, or multivalent ions, since these tend to interfere with the desired redox reaction between antimony and vanadium.

Thus, according to the present invention the superior catalytic performance in paraffin ammoxidation is obtained with the catalysts of the invention which contain a complex vanadium-antimony oxide composition with vanadium in a low oxidation state and antimony in a high oxidation state greater than $+3$, plus some excess antimony oxide as crystalline $Sb_2O_4$, plus an inorganic oxide support, as will be shown by comparative examples hereafter.

Whether or not tungsten is present in the catalysts shown in formula (1) of the catalysts of the invention, the promoting element Sn from the A Group and the promoting elements Te and Fe from the B Group give especially good results in the catalyst of the invention, either when one or any two or three of these elements are present.

Thus, an especially useful group of complex metal oxide catalysts of the invention for use in the paraffin ammoxidation process of the invention are the essentially bismuth free catalysts having the elements and the proportions which are represented by the formula $$VSb_mA_aB_bO_x \qquad \text{formula (3)}$$

where
A is one or more of W and Sn;
B is one or more of Fe and Te; and
where m is greater than 1 and up to 20 (usually 2–10, most usually 3–7); a is 0–10; b is 0–5; a is equal to or less than m; b is equal to or less than m and usually is at least 0.2; wherein x is determined by the oxidation state of the other elements; and wherein the antimony has an average valency higher than $+3$ and the vanadium has an average valency lower than $+5$, wherein crystalline $Sb_2O_4$ is present in said catalyst, and wherein the foregoing catalyst is on a inorganic oxide support material. Now preferred support materials are silica-alumina and alumina as previously discussed herein.

In formulas (1) and (3) subscript a usually is at least 0.2, more usually at least 0.4 or 0.5. In formula (1) at least 0.2 atoms of W are usually present per atom of V, and the total of W plus Sn atoms (if any Sn is present) is usually at least 0.4 atoms. The same is true of formula (3).

Especially useful catalyst compositions of the foregoing description are those in which a is at least 1 and includes at least 1 atom of W.

The optional elements shown in formulas (1) and (3) are incorporated in the base vanadium/antimony/support precursor slurry or are added to the solids recovered from the slurry by methods generally known in the art, using oxides, hydroxides, acids, salts (particularly organic salts such as acetates), and other comounds of such elements. Examples of such incorporation are shown in the specific examples hereinafter.

Tungsten is advantageously incorporated as ammonium meta- or orthotungstate, tungstic acid, or tungsten trioxide.

The catalyst support not only improves mechanical stability of the catalysts, but the catalytic activity is significantly improved, especially in the case of alumina and silica-alumina. This is amply shown in the examples. Besides alumina and silica-alumina other supports that can be used are silica, titania, silica-titania, $Nb_2O_5$, $AlPO_4$, silica-niobia, silica-zirconia, zirconia, and magnesia, etc.

Now preferred support materials for not only improving mechanical stability but also for improving the yield of the desired nitriles are selected from silica-alumina and alumina having 20–100, usually 50–100, preferably 60–100 weight percent alumina; silica-titania and titania having 20–100 weight percent titania; silica-zirconia and zirconia having 80–100 weight percent zirconia; and silica-niobia and niobia having 30–100 weight percent niobia ($Nb_2O_5$).

The weight ratio of the catalyst having the ingredients of empirical formulas (1) or (3) to the support material can vary from 9:1 to 1:9.

In the ammoxidation of the present invention, the reaction is preferably carried out in the gas phase by contacting a mixture of the paraffin, ammonia and a molecular oxygen containing gas, such as air, with a catalyst of the invention contained in a fixed bed, a gravity flowing bed, a fluidized bed or a fast transport reactor mode. It also possible to include additional diluents such as steam, nitrogen, carbon dioxide or helium.

The mole ratio of oxygen to the paraffin, such as propane, can vary from 0.5:1 to 4:1, and a ratio in the range from 1:1 to 3:1 is usual. The ammonia to paraffin (such as propane) ratio can vary from 0.5:1 to 5:1, but is usually from 1:1 to 5:1. When ammonia to paraffin ratios are much less than 1, various undesirable oxygenated derivatives of the paraffin can be formed.

The reaction temperature can vary from 400° to 650° C., but is usually 460° to 520° C. The latter temperature ranges are especially useful in the case of propane ammoxidation to acrylonitrile.

The average contact time can be from 1 to 20 seconds, but is usually from 2 to 8 seconds.

The catalysts of the present invention are believed to be unique. U.S. Pat. No. 3,860,534, 1975, describes catalysts that contain both vanadium and antimony but these are both in a high oxidation state and are thus entirely different from the catalysts of the present invention.

The following examples of the invention are exemplary and should not be taken as in any way limiting.

In the examples the conversion, yield and selectivity are defined as follows:

$$\text{conversion} = \frac{\text{moles paraffin reacted}}{\text{moles paraffin charged}} \times 100\ (\%)$$

$$\text{yield} = \frac{\text{moles product produced}}{\text{moles paraffin charged}} \times 100\ (\%)$$

$$\text{selectivity} = \frac{\text{moles product produced}}{\text{moles paraffin reacted}} \times 100\ (\%)$$

The term per pass conversion when used herein has the same definition as yield.

EXAMPLE 1

A catalyst having the composition 50% $VSbO_x$+50% $SiO_2$ was prepared as follows. In a flask equipped for heating under reflux with agitation there was placed 100g. of 40 percent silica sol with 30 ml additional water, and 24.6g. $Sb_2O_3$. To this mixture there was added a hot solution of 19.8g. $NH_4VO_3$, and the slurry was stirred and boiled under reflux for 12-16 hours to effect the redox reaction between vanadium and antimony. It was then transferred to an open beaker and heated with stirring on a hot plate to remove the bulk of the water. The resulting wet product was dried in air overnight at 110°-120° C., then further heated at 350° C. for 5 hours, screened to the desired particle size and calcined in air at 530° C. for 3 hours. A sample of the finished catalyst was subjected to x-ray diffraction analysis. The XRD diagram obtained was identical to that published by Berry et al. in the references quoted earlier.

EXAMPLE 2

A catalyst having the composition 50% $VSbWO_x$+50% $SiO_2$ was prepared similarly to that of Example 1 from 100g. 40% silica sol, 12.4g. $Sb_2O_3$, and 10.0g. $NH_4VO_3$, but after the redox reaction, 23.0g. ammonium metatungstate in 50 ml $H_2O$ was added to the mixture. The evaporation, drying and calcination were then conducted in the same manner as in Example 1.

EXAMPLES 3-14

Additional catalysts, listed in Table I, were prepared according to examples 1 and 2, but with varying ratios of V, Sb, and W. Catalysts supported on silica-alumina were made by substituting hydrated alumina (85% as $Al_2O_3$) for part of the 40 percent silica sol, the total amount of support remaining at 50 wt. percent. In some catalysts, $V_2O_5$ was used as vanadium source instead of $NH_4VO_3$. The catalysts were tested for performance in propane ammoxidation using a fixed bed 5 cc. microreactor with a preheat leg immersed in a temperature-controlled molten salt bath. The reaction feed (propane, ammonia, air) was metered through mass flow controllers into a mixing column, then introduced into the bottom of the reactor through the preheat leg. As an additional diluent (optional) water was fed through a septum at the top of the preheat leg, using a syringe pump. The catalyst charge was 5 cc of 20-35 mesh particles in a fixed bed reactor. The reaction temperature was 500° C., and the total feed flow was such as to obtain an average contact time of 4.5 seconds. The feed ratios are listed with the results in the following Tables. The effluent from the reactor ws recovered and analyzed, and the amounts of acrylonitrile, by-products and unreacted feed determined. The results for catalysts of Examples 1-14 are listed in Table I. Since HCN is a valuable co-product of acrylonitrile production, its yields and selectivities are included.

The above examples show that vanadium antimonates exhibit significant catalytic activity in the production of acrylonitrile by ammoxidation of propane. They also show the significant effects of the excess antimony, the catalyst support, and the presence of tungsten on the catalytic performance, and the performance variations with reaction conditions (e.g. $O_2/C_3$ ratio). Examples No. 9 and 10 illustrate different sources of vanadium that can be used. As comparative examples, Examples No. 4 and 7 show the importance of the oxidation of the excess antimony oxide present in the catalyst to an oxidation state greater than +3. Note that all catalysts of the invention herein contained crystalline $Sb_2O_4$, while examples 4 and 7 did not.

EXAMPLES 15-25

To show the effect of addition of one or more additional elements to the catalysts of this invention, catalysts listed in Table II were prepared according to procedures of Examples No. 1 and 2. The additional elements were incorporated after the completion of the redox reaction of $Sb_2O_3$ with $NH_4VO_3$ or $V_2O_5$. By way of illustration, tellurium was added as $TeO_2$, tin as aqueous 18 percent $SnO_2$ sol, and iron as ferrous acetate. The catalysts were supported on silica-alumina (as in Examples 5-14), except for Example 23 where silica-titania was used. The catalysts were tested as already described, the results are shown in Table II.

EXAMPLES 26-29

To show the importance of forming a vanadium antimonate via a redox reaction between trivalent antimony and pentavalent vanadium, a catalyst having the empirical formula of the catalyst of Example 19 ($VSb_5W_{0.5}Fe_{0.5}Te_{0.5}O_x$) was prepared as follows.

To a warm slurry of 37.5 Catapal SB hydrated alumina, AlO(OH), and 20.0g. 40% silica sol in water, there was added a hot solution of 4.12g. $NH_4VO_3$ in 100 ml $H_2O$, followed by 237.5g. of aqueous 12% $Sb_2O_5$ sol (containing 28.5g. $Sb_2O_5$). To this mixture there was added 4.75g. ammonium metatungstate in 10 ml $H_2O$, 2.81g. $TeO_2$, and 7.12g. $Fe(NO_3)_2$ $9H_2O$ in 15 ml $H_2O$. The mixture was boiled down, with agitation, to a paste, dried overnight at 115°-20° C., treated 5 hours at 350° C., screened and calcined for 3 hours at 530° C.

In the same manner, but without the additional elements, a catalyst having the empirical formula of the catalyst of Example 6 ($VSb_5O_x$) was also made. Both catalysts were tested in the described manner; the results are shown in Table III.

In the above comparative examples the catalysts were prepared in such a manner that a redox reaction between antimony and vanadium to form a vanadium antimonate could not take place, and both elements remained in a high oxidation state. A comparison of the results of Table III with the corresponding results of Examples 6, 8, 19 and 20 show clearly that the catalysts of this invention are greatly superior to those of Table III, producing much higher product yields and selectivities. At conditions of increased oxygen/propane ratio where the performance of the catalysts of this invention is further improved, the catalyst of the comparative examples 28 and 29 becomes even worse.

The excellent results shown by the examples of the invention that are in Tables I, II and III are, furthermore, achieved by using surprisingly low calcination temperatures in catalyst preparation, in contrast to other vanadium-antimony compositions described in the prior art.

EXAMPLES 30-41

To show the specific effect of the support or catalyst performance, in addition to its normal function to give physical strength and attrition resistance, the runs shown in Table IV were carried out.

TABLE I

Ammoxidation of Propane

Temp.: 500° C.
Contact time: 4.5 sec  50 wt. % catalyst support
Feed ratio: $C_3/NH_3/O_2/N_2/H_2O$ = 1/2/1.5(2.0)/5.7(7.5)/3   Calcination @ 530° C. in air or $N_2$

| Example No. | Catalyst[1] | Support[1] | Source | Calcination | $O_2/C_3$ | % Conv $C_3$ | % select. AN | % select. HCN | % yield AN | % yield HCN |
|---|---|---|---|---|---|---|---|---|---|---|
| 1 | $VSbO_x$ | $SiO_2$ | $NH_4VO_3$ | AIR | 1.5 | 15.4 | 23.3 | 13.6 | 3.6 | 2.1 |
| 3 | $VSb_5O_x$ | $SiO_2$ | $NH_4VO_3$ | AIR | 1.5 | 21.6 | 43.5 | 16.0 | 11.6 | 4.3 |
| 4 | " | $SiO_2$ | $NH_4VO_3$ | $N_2$ | 1.5 | 3.4 | 32.9 | 22.5 | 1.1 | 0.8 |
| 2 | $VSbWO_x$ | $SiO_2$ | $NH_4VO_3$ | AIR | 1.5 | 14.7 | 29.8 | 14.7 | 4.4 | 2.2 |
| 5 | $VSbO_x$ | SIAL | $NH_4VO_3$ | AIR | 1.5 | 39.3 | 44.3 | 5.4 | 17.4 | 2.1 |
| 6 | $VSb_5O_x$ | SIAL | $NH_4VO_3$ | AIR | 1.5 | 47.6 | 44.4 | 1.4 | 20.5 | 0.7 |
| 7 | " | SIAL | $NH_4VO_3$ | $N_2$ | 1.5 | 27.6 | 19.1 | 5.7 | 5.3 | 1.6 |
| 8 | " | SIAL | $NH_4VO_3$ | AIR | 2.0 | 63.6 | 46.8 | 7.2 | 29.6 | 4.6 |
| 9 | " | SIAL | $V_2O_5$ | AIR | 1.5 | 43.9 | 47.7 | 1.4 | 20.9 | 0.6 |
| 10 | " | SIAL | $V_2O_5$ | AIR | 2.0 | 64.0 | 45.6 | 2.2 | 29.2 | 1.4 |
| 11 | $VSbWO_x$ | SIAL | $NH_4VO_3$ | AIR | 1.5 | 32.8 | 29.8 | 2.2 | 9.8 | 0.7 |
| 12 | $VSb_5W_{0.5}O_x$ | SIAL | $NH_4VO_3$ | AIR | 1.5 | 50.0 | 51.2 | 3.7 | 25.6 | 1.9 |
| 13 | $VSb_5WO_x$ | SIAL | $NH_4VO_3$ | AIR | 1.5 | 46.9 | 53.3 | 4.4 | 25.0 | 2.1 |
| 14 | " | SIAL | $NH_4VO_3$ | AIR | 2.0 | 73.3 | 52.4 | 7.8 | 38.4 | 5.7 |

[1]SIAL = silica-alumina having 20% $SiO_2$ and 80% $Al_2O_3$

TABLE II

Ammoxidation of Propane

Temp.: 500° C.   catalyst support: 50% silica-aluminia
Contact time: 4.5 sec   (20% $SiO_2$, 80% $Al_2O_3$)
Feed ratio: $C_3/NH_3/O_2/N_2/H_2O$ = 1/2/1.5(2.0)/5.7(7.5)/3  calcination: @ 530° C. in air

| Example No. | Catalyst[1] | Source | $O_2/C_3$ | % Conv. $C_3$ | % select. AN | % select. HCN | % yield AN | % yield HCN |
|---|---|---|---|---|---|---|---|---|
| 15 | $VSb_5TeO_x$ | $NH_4VO_3$ | 1.5 | 44.1 | 46.3 | 0.3 | 20.4 | 0.1 |
| 16 | $VSb_5SnO_x$ | $NH_4VO_3$ | 1.5 | 29.3 | 41.0 | 1.5 | 16.1 | 0.6 |
| 17 | $VSb_5Te_{0.5}Sn_{0.5}O_x$ | $NH_4VO_3$ | 1.5 | 41.0 | 53.2 | 3.4 | 21.8 | 1.4 |
| 18 | $VSb_5W_{0.5}Fe_{0.5}O_x$ | $NH_4VO_3$ | 1.5 | 46.5 | 45.7 | 6.5 | 21.3 | 3.0 |
| 19 | $VSb_5W_{0.5}Fe_{0.5}Te_{0.5}O_x$ | $NH_4VO_3$ | 1.5 | 49.7 | 53.3 | 5.5 | 26.5 | 2.7 |
| 20 | " | $NH_4VO_3$ | 2.0 | 66.1 | 48.1 | 7.0 | 31.8 | 4.6 |
| 21 | " | $V_2O_5$ | 1.5 | 39.9 | 56.1 | 3.9 | 22.4 | 1.6 |
| 22 | " | $V_2O_5$ | 2.0 | 65.8 | 50.6 | 6.4 | 33.3 | 4.2 |
| 23 | $VSb_5W_{0.5}Fe_{0.5}Te_{0.5}O_x$[1] | $NH_4VO_3$ | 2.0 | 42.5 | 53.3 | 1.7 | 22.7 | 0.7 |
| 24 | $VSb_5W_{0.5}Te_{0.5}Sn_{0.5}O_x$ | $NH_4VO_3$ | 1.5 | 51.1 | 59.1 | 3.6 | 30.2 | 1.8 |
| 25 | " | $NH_4VO_3$ | 2.0 | 68.8 | 56.7 | 5.9 | 30.0 | 4.1 |

[1]Supported on 50% silica-titania (20% $SiO_2$, 80% $TiO_2$)

TABLE III

Ammoxidation of Propane

Temp.: 500° C.
Contact time: 4.5 sec   catalyst support: 50% silica-alumina
Feed ratio: $C_3/NH_3/O_2/N_2/H_2O$ =   (20% $SiO_2$, 80% $Al_2O_3$)
1/2/1.5(2.0)/5.7(7.5)/3   calcination: @ 530° C. in air

| Example No. | Catalyst[1] | $O_2/C_3$ | % Conv. $C_3$ | % select. AN | % select. HCN | % yield AN | % yield HCN |
|---|---|---|---|---|---|---|---|
| 26 | $VSb_5O_x$ | 1.5 | 42.2 | 39.3 | 3.5 | 16.6 | 1.5 |
| 27 | " | 2.0 | 60.0 | 37.0 | 2.6 | 22.2 | 1.6 |
| 28 | $VSb_5W_{0.5}Fe_{0.5}Te_{0.5}O_x$ | 1.5 | 37.9 | 44.7 | 5.7 | 16.9 | 2.2 |
| 29 | " | 2.0 | 45.0 | 29.3 | 1.5 | 13.2 | 0.7 |

TABLE IV

AMMOXIDATION OF PROPANE

| Example No. | Catalyst | \multicolumn{5}{c}{Support Composition wt. %} | $O_2/C_3$ | % Conv. $C_3$ | % Yield AN |
|---|---|---|---|---|---|---|---|---|---|
| | | $SiO_2$ | $Al_2O_3$ | $TiO_2$ | $ZrO_2$ | $Nb_2O_5$ | | | |
| 30 | $VSb_5O_x$ (no support) | 0 | 0 | 0 | 0 | 0 | 1.5 | 31.8 | 10.1 |
| 31 | $VSb_5O_x$ (no support) | 0 | 0 | 0 | 0 | 0 | 2.0 | 40.0 | 11.5 |
| 32 | $VSb_5O_x$ | 100 | 0 | 0 | 0 | 0 | 1.5 | 26.6 | 11.6 |
| 33 | $VSb_5O_x$ | 20 | 80 | 0 | 0 | 0 | 1.5 | 49.3 | 24.7 |
| 34 | $VSb_5O_x$ | 20 | 80 | 0 | 0 | 0 | 2.0 | 63.3 | 29.6 |
| 35 | $VSb_5O_x$ (no support) | 0 | 0 | 0 | 0 | 0 | 2.0 | 42.9 | 11.2 |
| 36 | $VSb_5WO_x$ | 100 | 0 | 0 | 0 | 0 | 2.0 | 45.8 | 11.8 |
| 37 | $VSb_5WO_x$ | 20 | 80 | 0 | 0 | 0 | 2.0 | 66.7 | 40.0 |
| 38 | $VSb_5WO_x$ | 80 | 20 | 0 | 0 | 0 | 2.0 | 48.3 | 22.2 |
| 39 | $VSb_5WO_x$ | 80 | 0 | 20 | 0 | 0 | 2.0 | 42.4 | 19.9 |
| 40 | $VSb_5WO_x$ | 15 | 0 | 0 | 85 | 0 | 2.0 | 31.1 | 17.0 |
| 41 | $VSb_5WO_x$ | 46 | 0 | 0 | 0 | 54 | 2.0 | 44.3 | 18.9 |

Conditions:
$C_3/NH_3/O_2/N_2H_2O$ = 1/2/1.5(2)/5.7(7.5)/3
Temperature 500° C.
Contact Time 4.5 Sec.

[1] In all supported catalysts in Tables I–IV the support was 50 weight percent of the total catalyst composition

EXAMPLE 42

In this example the catalyst was $VSb_5WO_x$ supported on an equal weight of alumina. The catalyst charge was 5 cc of 20–35 mesh particles in the fixed bed reactor. The feed ratios were Propane /$NH_3$ / $O_2$ / $N_2$ / $H_2O$ = 1 / 2 / 2 / 7.5 / 3.1

The reaction temperature was 500° C. and the contact time was 4.4 seconds. The molar ratio of $O_2$ to $C_3$ (propane) was 2. The propane conversion was 65.2 percent and the yields and selectivities were as shown in Table V:

TABLE V

| | % Yield | % Selectivity |
|---|---|---|
| Acrylonitrile | 25.8 | 39.6 |
| HCN | 4.3 | 6.6 |

The catalyst for this example was prepared as follows:

A catalyst having the compositin 50% $VSb_5WO_x$ + 50% $Al_2O_3$ was prepared as follows. In a flask equipped for heating under reflux there was placed 150 ml water and 5.4 $NH_4VO_3$. The mixture was stirred and heated until a clear solution was obtained, then 33.6 g $Sb_2O_3$ was added. The resulting slurry was stirred and boiled under reflux for 12–16 hours to effect the redox reaction between vanadium and antimony, in a manner similar to that shown in Example 1. It was then transferred to an open beaker and heated with stirring. A solution of 12.45 g ammonium meta-tungstate in 25–30 ml water was added, and the heating and stirring continued to remove the bulk of the water. The resulting wet product was dried in air overnight at 110°–120° C. It was then ground to a fine powder and thoroughly mixed with 58.8 g hydrated alumina (85% $Al_2O_3$, tradename Catapal SB). This mixture was stirred with 64-65 ml water in which 7.5 ml acetic acid had been dissolved and then kneaded thoroughly until a semi-solid mass having the consistency of wet dough was obtained. This product was dried at 100°–120° C. then further heated at 350° C. for 5 hours, screened to a desired particle size, and calcined in air at 610° C. for 3 hours.

EXAMPLES 43–45

The same catalyst was used in these examples as in Examples 13 and 14, but in the fixed bed ammoxidation of isobutane. Conditions and results are shown in Table VI.

TABLE VI

Ammoxidation of Isobutane
Temp.: 500° C.
Contact time: 4.5 sec
Feed ratio: $C_4/NH_3/O_2/N_2/H_2O$ = 1/2/2/7.5/3
catalyst support: 50% silica-aluminia (20% $SiO_2$, 80% $Al_2O_3$)
calcination: σ 530° C. in air

| Example No. | Catalyst[1] | Isobutane % Conv. | % Yield MAN | % Yield AN | % Yield HCN | % Selectivity MAN | % Selectivity AN | % Selectivity HCN |
|---|---|---|---|---|---|---|---|---|
| 43 | $VSb_5WO_x$ | 40.5 | 6.4 | 3.2 | 2.9 | 15.9 | 3.2 | 7.2 |
| 44 | $VSb_5WO_x$ $C_4/NH_3/O_2/H_2O$ = 1/2/3/11.3/1.5 Contact time: 3.7 sec. | 41.3 | 8.8 | 3.2 | 2.4 | 21.2 | 7.7 | 5.8 |
| 45 | $VSb_5WO_x$ | 39.3 | 4.0 | 2.6 | 2.5 | 10.1 | 6.5 | 6.4 |

MAN is methacrylonitrile
AN is acrylonitrile

In all of the ammoxidation runs herein air was the source of oxygen. When 2 moles of $O_2$ were used per mole of propane ($C_3$), the nitrogen automatically increased to 7.5 moles.

As will be evident to those skilled in the art, various modifications of this invention can be made or followed in the light of the foregoing disclosure and discussion without departing from the spirit and scope of the disclosure or from the scope of the claims.

We claim:

1. A complex metal oxide catalyst, which is essentially free of bismuth, having the elements and the proportions which are represented by the following empirical formula:

where

A is one or more of W, Sn, B, Mo and Ge and includes at least 0.2 atoms of W per atom of V;

B is one or more of Fe, Co, Ni, Cr, Mn, Zn, Se, Te and As;

C is one or more of an alkali metal, Ca, Sr, Ba, Tl and where m is greater than 1 and up to 20; a is 0.4–10; b is 0–5; c is 0–1; a is equal to or less than m; b is equal to or less than m; wherein x is determined by the oxidation state of the other elements present, and wherein the antimony has an average valency higher than +3 and the vanadium has an average valency lower than +5, wherein crystalline $Sb_2O_4$ is present in said catalyst, and wherein the foregoing catalyst is on an inorganic oxide support material selected from alumina and silica-alumina which is 50 to 100 weight percent alumina.

2. A catalyst of claim 1 wherein m is 2–10.

3. A catalyst of claim 1 wherein m is 3–7.

4. A catalyst of claim 1 wherein A includes at least 0.2 atoms of W per atom of V and the total A atoms include at least 0.4 (W atoms + Sn atoms) per atom of V.

5. A catalyst of claim 4 wherein b is at least 0.2.

* * * * *